United States Patent [19]
Sjöström

[11] Patent Number: 5,685,317
[45] Date of Patent: Nov. 11, 1997

[54] APPARATUS FOR MEASURING CARDIAC SIGNALS, USING ACOUSTIC AND ECG SIGNALS

[75] Inventor: Svend-Olof Sjöström, Karup, Denmark

[73] Assignee: Bang & Olufsen Technology A/S, Struer, Denmark

[21] Appl. No.: 556,937

[22] PCT Filed: Jun. 1, 1994

[86] PCT No.: PCT/DK94/00212

§ 371 Date: Mar. 5, 1996

§ 102(e) Date: Mar. 5, 1996

[87] PCT Pub. No.: WO94/27497

PCT Pub. Date: Dec. 8, 1994

[30] Foreign Application Priority Data

Jun. 2, 1993 [DK] Denmark ................................ 0631/93

[51] Int. Cl.[6] ........................................................ A61B 5/02
[52] U.S. Cl. ................................................................ 128/715
[58] Field of Search ........................................ 128/715, 773

[56] References Cited

U.S. PATENT DOCUMENTS

| | | | |
|---|---|---|---|
| 4,362,164 | 12/1982 | Little et al. | 128/715 |
| 4,378,022 | 3/1983 | Suobank et al. | 128/715 |
| 4,428,380 | 1/1984 | Wong et al. | 128/715 |
| 4,446,872 | 5/1984 | Marsoner et al. | 128/715 |
| 5,002,060 | 3/1991 | Nedivi | 128/715 |
| 5,003,605 | 3/1991 | Phillipps et al. | 128/715 |
| 5,036,857 | 8/1991 | Semmlow et al. | 128/715 |
| 5,086,776 | 2/1992 | Fowler, Jr. et al. | 128/715 |
| 5,341,811 | 8/1994 | Cano | 128/696 |
| 5,492,129 | 2/1996 | Greenberger | 128/715 |

*Primary Examiner*—William E. Kamm
*Assistant Examiner*—George R. Evanisko
*Attorney, Agent, or Firm*—Antonelli, Terry, Stout & Kraus, LLP.

[57] ABSTRACT

An apparatus for measuring the cardiac valve function of a person by analyzing an acoustic signal from the heart. The acoustic signal is synchronized with the electrocardiographic signal obtained from the heart. In order to improve the signal-to-noise ratio of the input electrocardiographic signal, the mains-synchronous noise is subtracted from the input electrocardiographic signal. Before analysis of the acoustic signal, a weighting is performed, compensating for individual differences in, in particular, the layer of body fat.

6 Claims, 4 Drawing Sheets

APPARATUS FOR MEASURING CARDIAC SIGNALS, USING ACOUSTIC AND ECG SIGNALS

BACKGROUND OF THE INVENTION

The invention concerns an apparatus for measuring the function of a person's heart valve, the apparatus being of the kind which uses an acoustic signal from the person's cardiac function measured at the outside surface of the body.

When physicians listen to heart sounds by means of a stethoscope they listen, for example, for those sounds which are generated by the blood flowing from the heart into the aorta. Such sounds are caused by turbulence in the flow after passage of a heart valve, and the character of such a sound gives a good background for evaluating the properties of the heart. It has been shown to be desirable to be able to classify persons, with or without circulatory problems, into several groups, some of which contain persons who will have to be subjected to more thorough diagnosis. The classification alone requires vast experience on the part of the physician and becomes expensive to perform. Hence there is a need for a measuring apparatus which is capable of performing this classification.

The connection between heart sound measured on the outside of the body and those conditions of a heart which cause the heart sound is well known and is used by trained physicians based on experience with the stethoscope sound in the physician's ear. It has been recognized that certain forms of apparatus and signal processing may support the physician in his interpretation of the heart sound, and procedures are known in which sonograms are displayed on a screen or are printed out. Thus the interpreting by the physician is moved from being an auditory problem to being a visual problem in which characteristic patterns have to be recognized visually. Furthermore, with sonograms there is more time for analysis, since the analysis is no longer tied to a function in real time.

It has, however, turned out that the known techniques are too time consuming to be useful in other than purely experimental measuring situations, since the spectrum analysis that is used is dependent on integration over many heartbeats, because there are many outer influences on the measured signals and furthermore inter-cycle differences. The known techniques hence do not allow ordinary clinical use and are still dependent on learning complex pattern recognition.

SUMMARY OF THE INVENTION

It is a purpose of the invention to provide an apparatus which is simple to use and which gives a large certainty for correct identification of the heart valve function. This is provided in the present invention by an apparatus which comprises a measuring microphone with a preamplifier, a preemphasis filter for compensating for the degree of obesity of the person, a spectrum analyzer which determines the relative energy distribution in at least one lower and at least one higher frequency range, where those parts of the acoustic signal which are to be analyzed are synchronized by means of a signal which is derived from electrocardiographic signals from the person, with or without a time delay.

It has been recognized in the invention that only through cooperation between a number of techniques for signal extraction and noise reduction, both for acoustic noise and electric and electromagnetic noise, is it possible to provide an apparatus which functions without the need for human intervention to reject irrelevant information.

In a preferred embodiment, in order to extract without time delay a synchronizing signal from the electrocardiographic signals, a non-recursive predictor for noise signals of the electrical mains frequency and its harmonics is used, and the noise signals are subtracted from the amplified electrocardiographic signal, followed by detection based on pattern recognition of the temporal placement of the QRS complex in the electrocardiograph signal that has thus been cleaned of noise.

Stethoscopes as well as microphones or accelerometers placed on the chest collect signals which have been filtered by tissue, in particular fatty tissue, which is interspersed between the sound source, in this case the heart, and the receiver. The signals are weak, and it is necessary to perform heavy digital signal processing in order to obtain reliable results. The signal from the source, i.e. the turbulent flow of blood through a valve, is very broadband, and the average size of the vortices determines the relative content of the high frequency energy. It is hence important that the spectral distribution of the sound be transferred for measurement and classification with a signal-to-noise ratio which is as large as possible, and this is obtained by subjecting the directly measured signal to pre-emphasis before signal processing.

A further advantageous embodiment includes filtering with a pre-emphasis filter which has a bandwidth from 0 to 3 kHz, amplification at 0 dB to a particular corner frequency and increasing at a rate of between 15 and 40 dB per decade above this, with the corner frequency in the range of 30–150 Hz, preferably in the range of 80–120 Hz. The amplification for the filter used is chosen according to the build and obesity of the test person, with the steepest curve being chosen for a heavy and overweight person. For a skinny person a steepness of between 15 and 24 dB/decade, preferably 16–20 dB/decade is chosen, for a person of normal build between 25 and 35 dB/decade, preferably 26–30 dB/decade is chosen, and for a heavy and very obese person between 35 and 42 dB/decade, preferably between 36 and 40 dB/decade.

An important prerequisite for correct generation of a synchronizing signal based on electrocardiographic signals is that the electrocardiographic signals are themselves extracted correctly without disturbing signals. They are commonly swamped by noise signals which display periodicity. It is a well-known problem in the electronic measuring field that the desired signals are hidden in signals from strong noise sources, and numerous methods for separating the signals have been developed. Commonly known methods for separating signal from noise may be to work with narrow bandwidths, including techniques based on phase-locking to the desired signal. These are general methods which generally improve the signal-to-noise ratio. But in the present case the problem is not so much that the signal is weak in relation to thermic noise or weak in relation to the internal noise of the measuring equipment, but rather that directly interfering signals are present, which may in the worst case overload the measuring circuits. A common source for such interfering signals is radiation from the electrical mains, whereby the desired signals are superimposed with signals which are of the mains frequency, or its multiples, and which are composed with varying phase. In this case a commonly used method is to use a filter which has a stopband for frequency components which are harmonics of the mains frequency. Such filters have to be very narrowband, however, in order to influence the desired signal as little as possible, and thereby they have a large time constant so that their influence is noticed in the time function of the filtered signal instead. Furthermore the damping of the interfering signals is far from sufficient for use with e.g. biological signals. A method which increases the signal-to-noise ratio considerably is based on fundamental frequency extraction and an adaptive filter which is synchronized to the fundamental in order to obtain a synthetic error signal which is subtracted from the noisy signal, but inherent phase shifts only make a given construction suitable for a very stable electrical mains frequency.

In a further advantageous embodiment of the invention a circuit for extraction of weak signals by means of a predictor circuit provides a replica of the noise signal which in a subtraction circuit is subtracted from the total noisy signal in order to isolate the desired signal.

Further advantageously an embodiment may allow the predictor to be a linear non-recursive predictor.

In a further advantageous embodiment the predictor is constructed using a delay line with taps.

It has been found to be essential to use the whole QRS complex in the electrocardiograph for synchronization, even though the user of an apparatus according to the invention would perform a temporal shift of the instant of synchronization, because a correctly extracted time for the QRS complex causes a temporally very stable synchronization which is a prerequisite for the signal processing and weighting which follows. It is for this reason that a pattern-recognition type extraction of the QRS complex is used. The designation QRS is used in its usual meaning for the electrical signals which may be detected in relation to the closure of the mitral valves and the following opening of the aorta valve in the heart during the transition from one cycle to the next.

A mathematically optimal detection of the temporal placement of a QRS complex may be based on a cross correlation between an instantaneous electrocardiographic signal and a reference QRS complex, with the requirement that the electrocardiographic signal consist of a pure signal and possibly an uncorrelated noise component. For this reason it is an essential requirement that the input signal to the QRS complex identification have had the correlated interference (i.e. that displaying periodicity) removed by the previous step of extracting of the electrocardiographic signal proper. This has, however, been obtained by e.g. the predictor for the noise signal and subsequent subtraction discussed above.

An advantageous embodiment of the invention hence comprises a store, i.e. a storage or memory device, for storing a reference QRS complex, a correlator for cross correlation between an electrocardiographic signal and the reference QRS complex, an adaptive amplitude detector and a differentiator for determining the time of the appearance of the R peak in the electrocardiographic signal, whereupon a trigger signal is released for synchronization of the spectral analysis of the acoustic signal.

BRIEF DESCRIPTION OF THE DRAWINGS

The invention will be described in greater detail in the following, with reference to the drawing, in which.

DETAILED DESCRIPTION OF PREFERRED EMBODIMENTS

Figure 1:
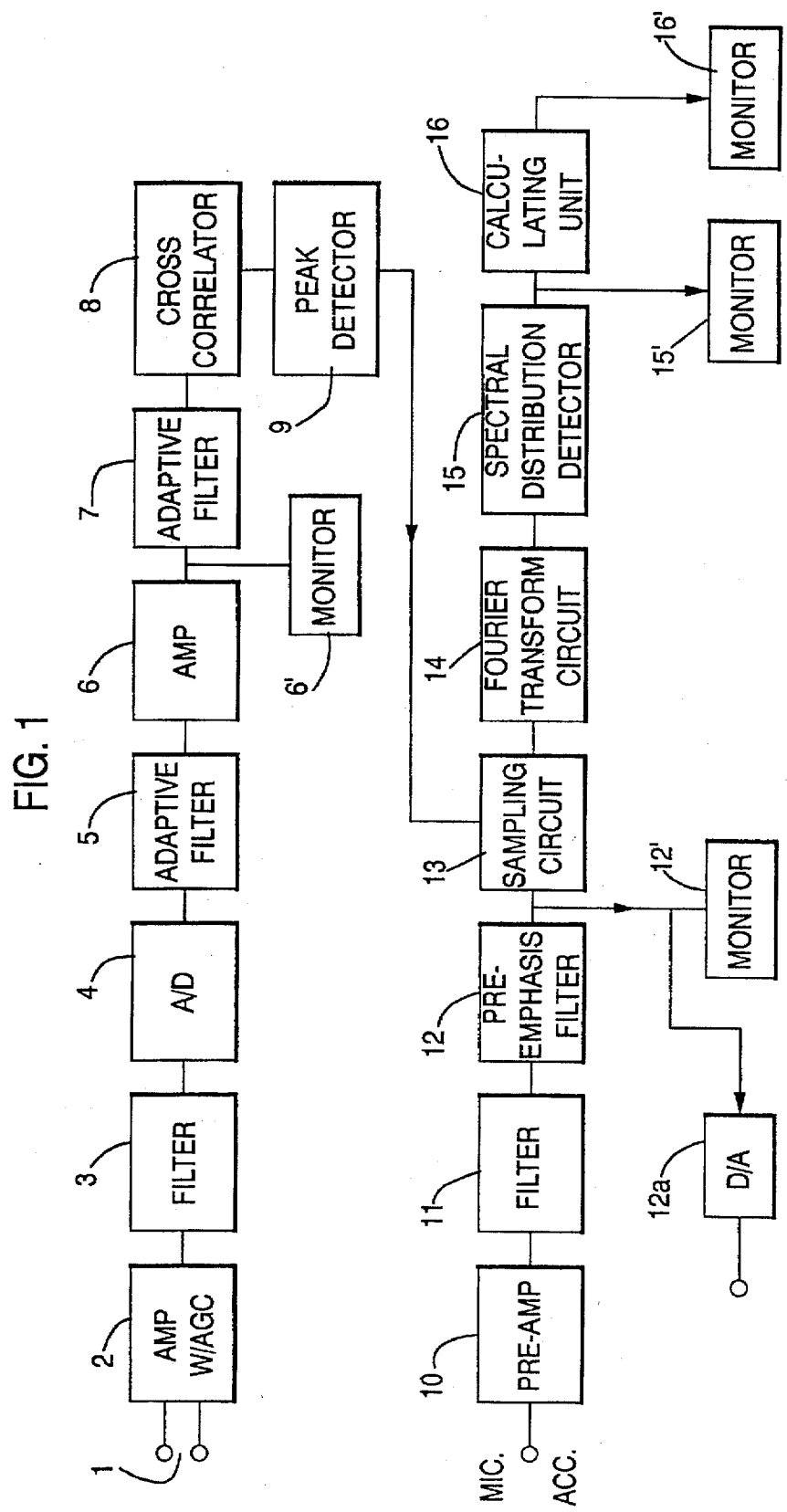
FIG. 1 shows an overall block diagram of an apparatus according to the invention.

In FIG. 1 are shown the connections for two electrodes 1 which are fitted on the person whose heart is to be examined. The principle of the invention allows the use of a two electrode ECG system which is a considerable simplification in comparison with the three-electrode system which was hitherto required. The ECG signal from the electrodes 1 is amplified in the analogue unit 2 in which there is also an automatic gain control. All other signal processing takes place in the digital domain, for which reason the signal is converted to digital representation after anti-aliasing filtering in filter 3. A digital filter with a low group delay restricts the frequency range to the minimum necessary because of the temporal resolution in analog-to-digital converter 4, and an adaptive filter 5 eliminates electrical mains frequency synchronous noise by means of a nonrecursive predictor for noise signals of the mains frequency or its harmonics which are subtracted from the amplified electrocardiographic signal. It has been determined to be advantageous to cascade this function, and hence the signal from the filter 5 is fed to an amplification control circuit 6 and to a filter 7, of the type of filter 5. After the amplification control circuit 6 there may be taken a signal which may be displayed on a monitor 6' as a representation of the time function of a de-noised ECG function. When in the present description the term "signal" is used, usually a digital representation is meant, in the form of tables of bytes which are treated by calculation according to modern signal processing techniques. This means that the functions take place in processors which are controlled by programs that are typically stored in programmable memories (PROM).

The signal after processing in filter 7 has obtained a considerably improved signal-to-noise ratio. Practical measurement has demonstrated that the signal following block 4 may have a ratio which is worse than between −20 and −60 dB, i.e. a signal which is totally swamped by interfering signals, while following filter 7 the ratio is better than +30 to +40 dB. Almost-all periodicity in the remaining signal has been removed through this treatment.

Figure 2:
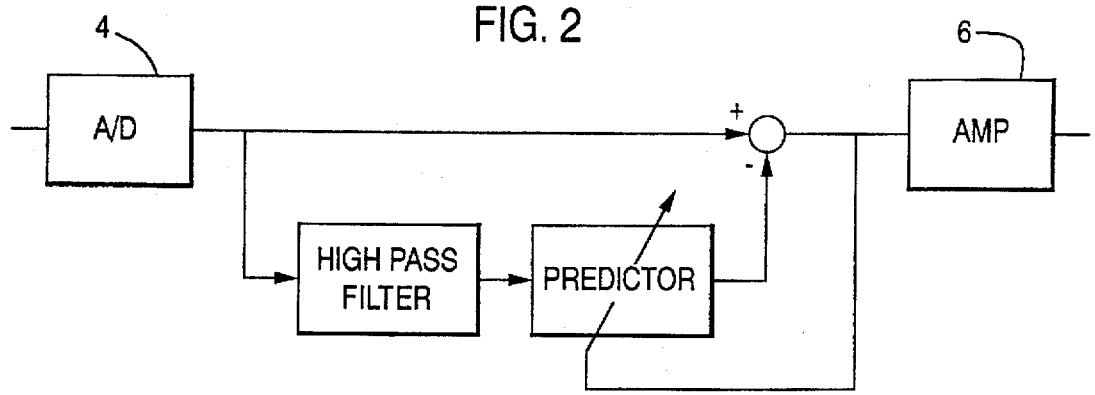
FIG. 2 shows a block diagram of the principle in a circuit for the elimination of mains frequency synchronous noise.
Figure 3:
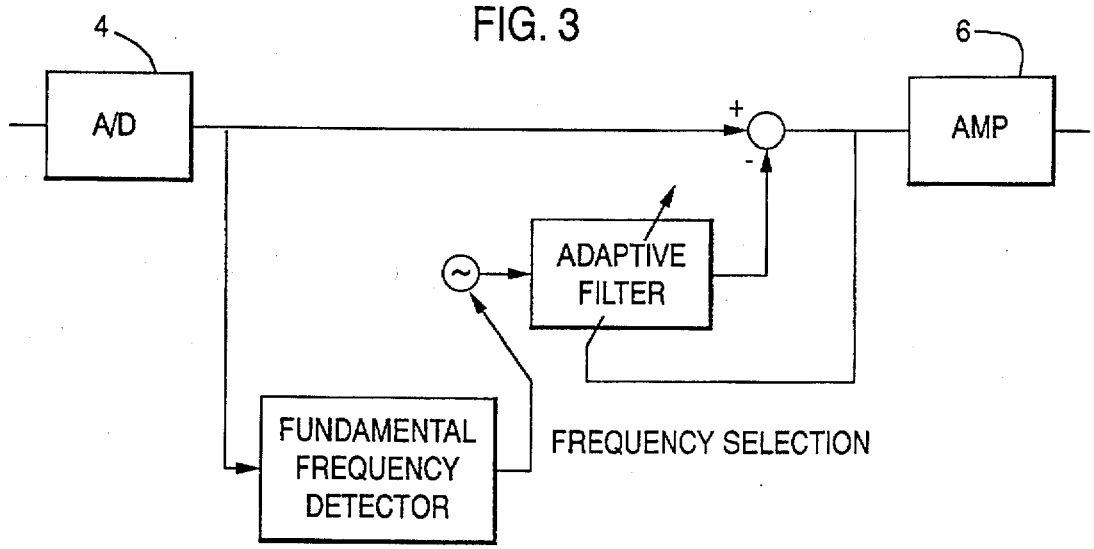
FIG. 3 shows an alternative system for the elimination of mains frequency synchronous noise.

It has been attempted to use two methods for removing interference from the electrical mains—on the one hand a predictor, and on the other fundamental frequency extraction and synthesis of a correction signal. The first method functions as a linear nonrecursive predictor, which may be of the tapped delay line or lattice type. At least two taps are used. The adaptation algorithm functions according to a principle where the energy in the desired signal is minimized, and this function principle is shown in FIG. 2. The other method detects the fundamental frequency of the electrical mains independently and controls a generator for a correction signal which is filtered in an adaptive filter so that its subtraction causes a reduction in the noise content in the desired signal, and this is shown schematically in FIG. 3. Both methods provide an excellent improvement in the signal-to-noise ratio, but the former can follow slow variations of the fundamental (frequency, phase, and amplitude), e.g. a frequency variation df/dt of 0.2 Hz/sec, and it also allows use of the apparatus with 50 or 60 Hz without adjustment. The latter can only follow small absolute frequency changes in the order of 0.1 Hz/sec.

Returning to FIG. 1, from the "clean" signal following filter 7 it is desired to extract a precise synchronizing signal for use with the selection of the acoustic signal to be processed. This occurs by detection of the QRS complex, and in this the precise determination of the instant of the occurrence of the maximum which is termed R. The traditional solution for obtaining a synchronizing signal or trigger signal from this complex is attributed to NASA and is based on an evaluation of the power spectral density, whereby the important information given by the phase is left out of consideration, causing an imprecise trigger signal. The traditional solution utilizes a second order band pass filter with a center frequency of 17 Hz and a Q equal to 3.3, followed by amplitude detection. Triggering occurs when the amplitude exceeds about 0.7 times the last trigger level.

Figure 4:
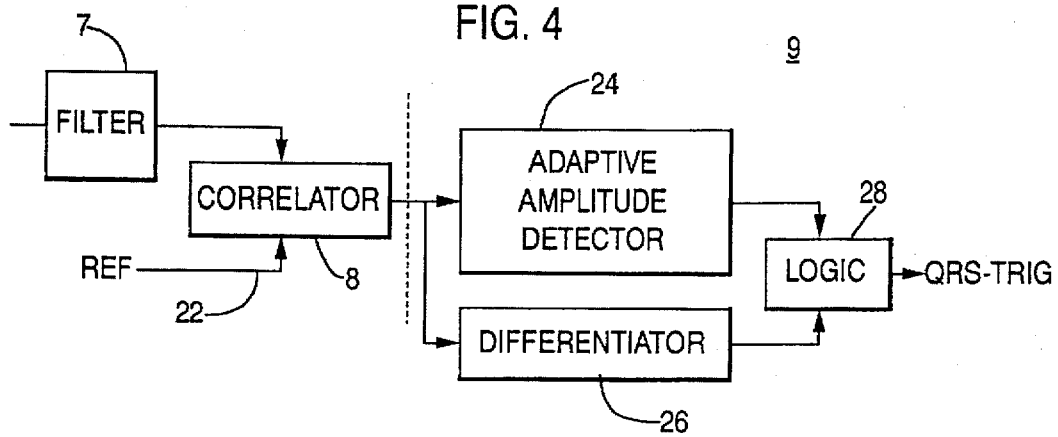
FIG. 4 shows a block diagram of the principle in a circuit for extraction of the time of the presence of a QRS complex.

According to the invention cross correlation between the instantaneous cleaned electrocardiographic signal and a reference QRS complex is used instead which gives an optimal detection of the instant QRS complex. This takes place in the chain of signal processing in cross correlator 8 followed by identification of R maximum in peak detector 9. This is shown schematically in greater detail in FIG. 4. The correlator performs as mentioned a cross correlation between the instantaneous ECG received from filter 7 and the reference QRS on line 22 which is obtained by continuously performing linear averaging of the QRS complexes obtained until then. Hence one may speak of an automatic learning function with respect to the specific person and/or measuring rig. At the start of the measurement cycle a previously stored complex is used, which has been obtained by averaging of a large number of typical complexes.

The output signal from the correlator 20 is applied to an adaptive amplitude detector 24 and a differentiator 26. The amplitude detector outputs a logical signal when the correlator's output signal exceeds a predetermined value which is held as a weighted previously measured value. The differentiator detects local maxima of the curve shape as a switch from a positive value to a negative value of the differentiated signal, and in case several such switches are obtained, a signal is given to the logic circuit 28 at the largest following upon a number of smaller. When both the amplitude condition and the local maximum conditions are met, a synchronization or trigger signal is delivered from peak detector 9.

Above has been described how one may, from a two electrode electrocardiographic signal, derive a precise synchronization signal for other signals obtained from the same source, i.e. a heart. These signals are acoustic or vibratory and are predominantly determined on the outside of the chest, but they may well be obtained by probes or catheters which have been led into cavities in the body. In case it is the outside of the chest which transmits the signals, it is relevant to use a microphone or an accelerometer for the reception. A microphone receives airborne sound and has hence to be shielded efficiently from the surroundings, while an accelerometer registers the surface movement of the chest, it being however a condition that its mass does not influence the measurement.

Figure 5:
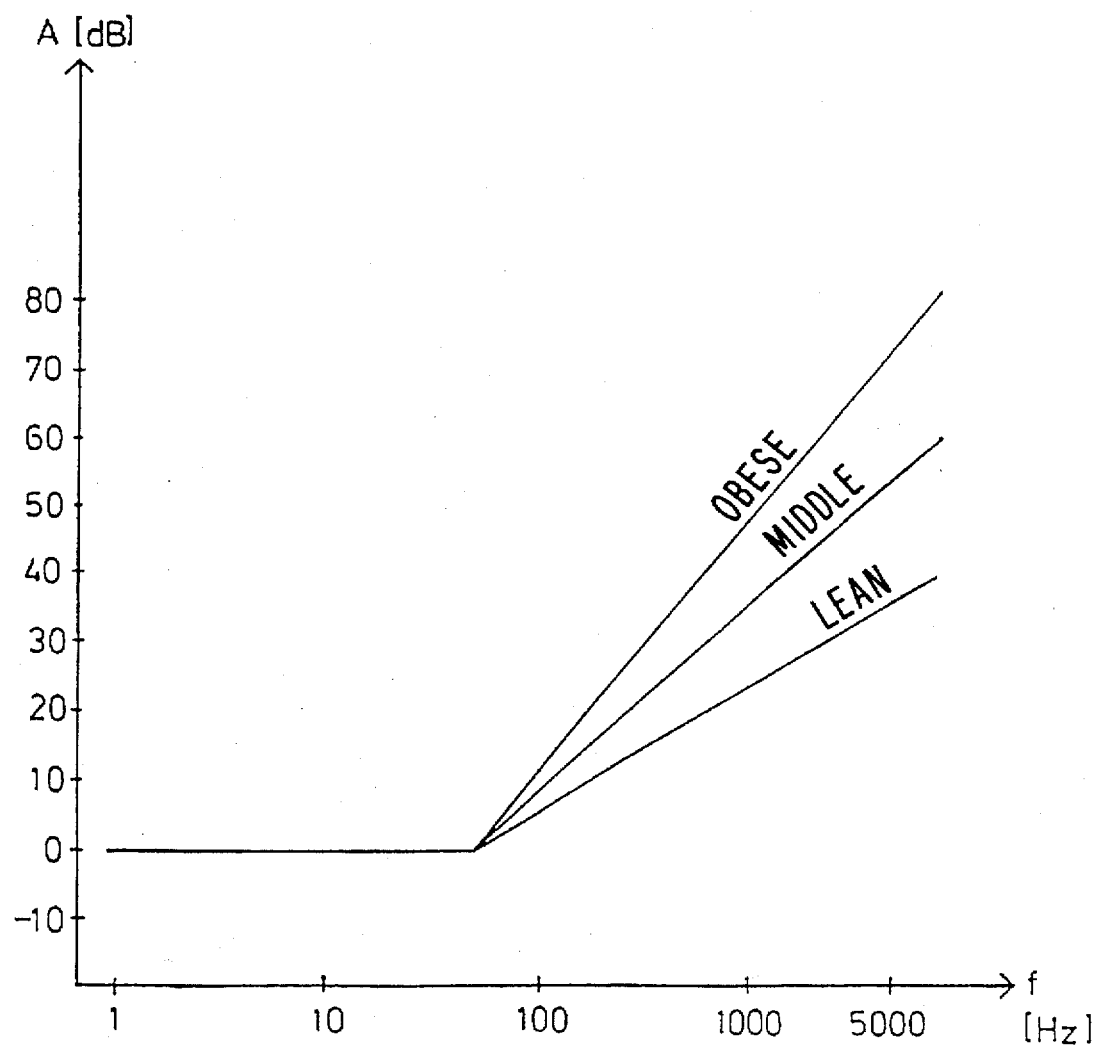
FIG. 5 shows the transfer function for a pre-emphasis filter according to the invention.

In FIG. 1 a microphone or accelerometer signal is fed to a preamplifier with an automatic amplification control 10, whereafter the analogue signal is converted to digital representation following anti-aliasing filtering in filter 11. The signal from the sound source itself, the flow through a heart valve to the aorta or another artery, is exposed to a severe modification because of the passage through fatty, bone, and muscle tissue. This will have the character of severe low pass-filtering. In order to compensate for this, a pre-emphasis is performed on the signal received in filter 12. It is a high pass filtering with typical transfer functions according to FIG. 5. Since the implementation is digital, it is comparatively simple to effect changes by ordinary programming, in case fairly uniform populations are to be classified.

In order to be able to treat a number of cycles of acoustical signals correctly in the evaluation of the relative energy distribution in a number of frequency bands, it is necessary to use time windows, and hence a synchronization which takes a sample of the time function in each cycle which as far as possible contains relevant information only. There must consequently not be added frequency components from the beginning and the end of a sample which are attributable to uncertainty in the occurrence of the beginning and the end, nor frequency components from the time function for the sampling itself, which is also termed the window function. A prerequisite for this is the precise synchronization pulse described above which has been obtained electrocardiographically. In sampling circuit 13 the discussed sampling of the pre-emphasized signal is performed. The selected data are processed by means of Fast Fourier Transformation in circuit 14, and the spectral distribution of the power is performed in circuit 15. As opposed to earlier thoughts, it is in the present case not a question of measuring the presence of specific characteristic frequencies in the measured signal, but rather of measuring the relative energy distribution in a lower frequency range and in a higher frequency range. A simple calculation of the energy at high frequencies in proportion to the energy at low frequencies is a good criterion for classifying a population, and this is performed in circuit 16.

Figure 6A:
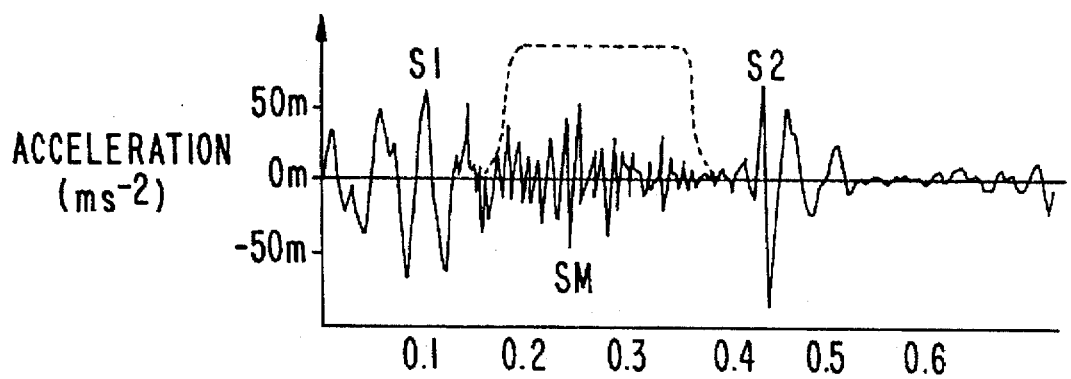
FIG. 6 shows the data which are used for the calculation of the degree of turbulence caused by faulty heart valves.
Figure 6B:
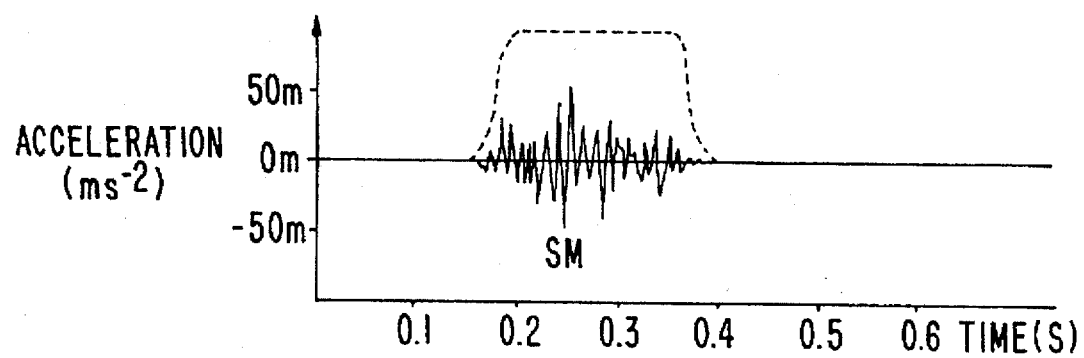
Figure 6C:
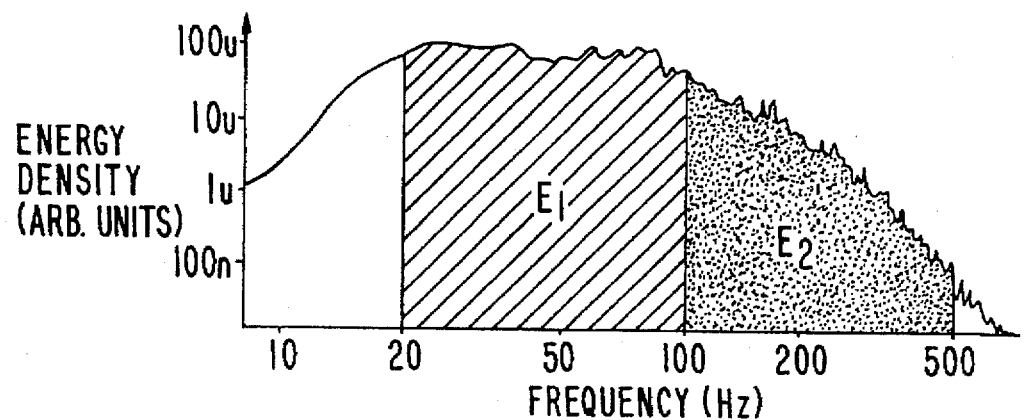

FIGS. 6a–6c show how the basis for this calculation is obtained. FIG. 6a shows a signal following filter 12, and FIG. 6b shows the corresponding signal following sampling circuit 13, with a suitable time delay in relation to the synchronization signal from peak detector 9 and with a time window of 150 milliseconds. FIG. 6c shows the averaged energy of such signals from more than 20 heart cycles following circuit 15. It is shown how, from the total frequency range from <<10 Hz and to 800 Hz, there has been taken a frequency range between 20 Hz and 500 Hz which is divided into two ranges at 100 Hz. The total energy in the area below 100 Hz, termed E1, is added to the total energy in the area above 100 Hz, termed E2, and the addition corresponds to the total energy in the whole frequency range 20 Hz to 500 Hz. The calculating unit 16 performs the calculation E2/(E1+E2). The result of this is a number as an expression of the character and degree of defects of the heart valve function. That number is displayed, typically on a monitor 16'. For practical reasons a double logarithmic scale has been used in FIG. 6(c).

In order that the apparatus may be used in conjunction with a specialist, signals following amplifier 6, filter 12, and circuit 15 are fed to monitors 6', 12', and 15', respectively, which display the temporal relationship between the electrocardiographic and the vibrationcardiographic functions. Furthermore a signal is taken following filter 12, passed through digital-to-analog converter 12a, and fed to headphones. Thus it becomes possible to hear a compensated (pre-emphasized) signal simultaneously with visual observation of the electrocardiograph and the acoustic function. Although not shown in the figure, it is possible to influence the time of synchronization by delaying it and by adjusting the width of the sampling in sampling circuit 13. These two adjustments are shown on the monitor as movement of two cursor lines. This enables the specialist to focus on those phenomena which are of the greatest relevance for a diagnosis. In order to document the performed measurement, the shown screen images may be printed on paper.

I claim:

1. An apparatus for the measurement of the heart valve function of a person's heart comprising a vibration transducer for detecting an acoustic signal at the outer surface of the person's body, a pre-emphasis filter for filtering the acoustic signal to compensate for the degree of obesity of the person, an input for receiving an input electrocardiographic signal from the person's body, an electronic circuit for obtaining a synchronizing signal from the input electrocardiographic signal, and a spectrum analyzer for determining the relative energy distribution in at least one lower and at least one higher frequency range, of the filtered acoustic signal the spectrum analyzer being synchronized by the synchronizing signal.

2. An apparatus according to claim 1, wherein the electronic circuit comprises a non-recursive predictor circuit for subtracting noise signals of the mains frequency and harmonics thereof from the amplified input electrocardiographic signal to provide a noise-reduced electrocardiographic signal, and a pattern detector for recognition of a temporal placement of the QRS complex in the noise-reduced electrocardiographic signal for providing the synchronizing signal.

3. An apparatus according to claim 2, wherein the predictor circuit provides a replica of the input electrocardiographic signal and includes a subtraction circuit for subtracting the replica from the input electrocardiographic signal.

4. An apparatus according to claim 3, wherein the predictor circuit comprises a linear non-recursive predictor and includes a delay line with taps.

5. An apparatus according to claim 2, further comprising a source of a reference QRS complex, a correlator for cross correlation between the noise-reduced electrocardiographic signal and the reference QRS complex, and an adaptive amplitude detector and a differentiator for providing the synchronization signal in response to the R peak in the noise-reduced electrocardiographic signal.

6. An apparatus according to claim 1, wherein the pre-emphasis filter has a bandwidth from 0 to 3 kHz, an amplification of 0 dB to a corner frequency and increases at a rate of between 15 and 40 dB per decade thereabove, and the corner frequency being in the range of 30–150 Hz.

* * * * *